United States Patent [19]

Sanders

[11] 4,031,752

[45] June 28, 1977

[54] WEB PROCESS CONTROL APPARATUS

[76] Inventor: Art Sanders, 230 Harvie Road, East, R.R. No. 5, Barrie, Ontario, Canada

[22] Filed: July 19, 1976

[21] Appl. No.: 706,226

[52] U.S. Cl. .................................. 73/159; 250/359; 356/199
[51] Int. Cl.² ........................................ G01N 33/34
[58] Field of Search ............. 73/159; 250/359, 569, 250/570, 571, 572; 356/199, 200, 203, 568

[56] References Cited

UNITED STATES PATENTS

| | | | |
|---|---|---|---|
| 3,190,261 | 6/1965 | Ziffer | 73/159 |
| 3,480,786 | 11/1969 | Kottman | 73/159 |

*Primary Examiner*—S. Clement Swisher
*Attorney, Agent, or Firm*—Robert D. Farkas

[57] ABSTRACT

This disclosure pertains to a web process control apparatus utilizing a pair of arms disposed parallel to one another and pivoted at a location outward from and adjacent to a marginal edge of a travelling flat web. Process control sensors detect various characteristics of the web and are located at each extreme free end of the arms. The web passes between opposed faces of the arms. The arms are pivoted in substantially ninety degree arcs along the surface of the web as the web moves in a direction parallel to the marginal edges thereof. The characteristics of the web to be measured is continuously scanned as the arms move in a prescribed controlled fashion, yielding in one direction, if so desired, a linear measurement transverse to the direction of web travel.

4 Claims, 4 Drawing Figures

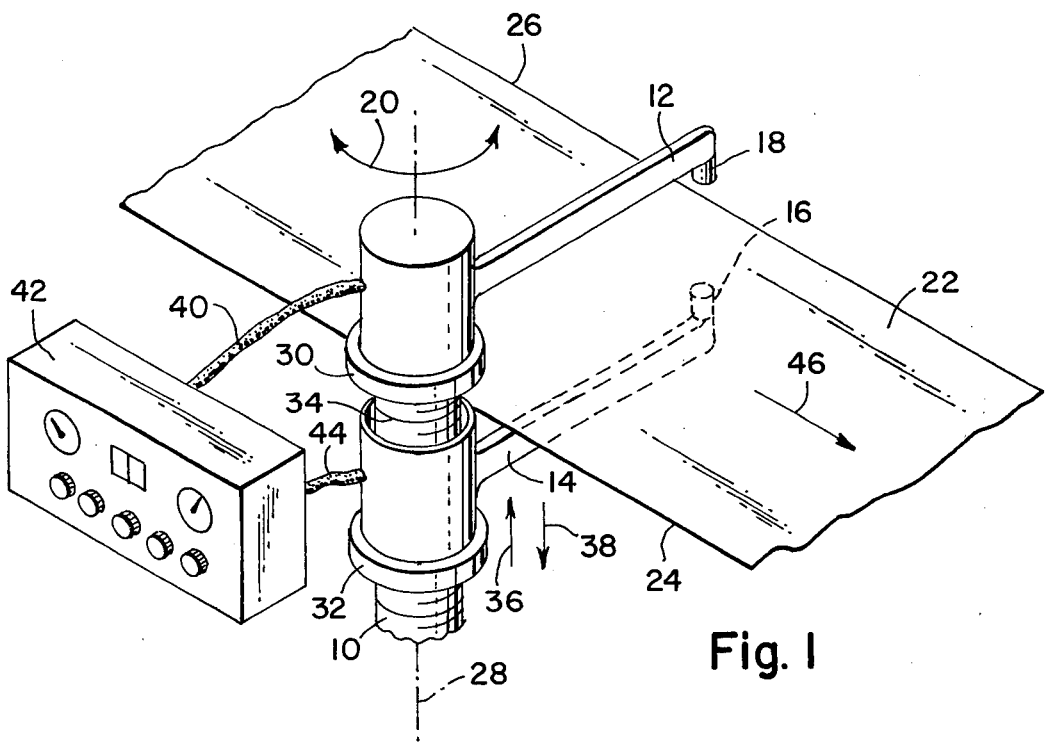
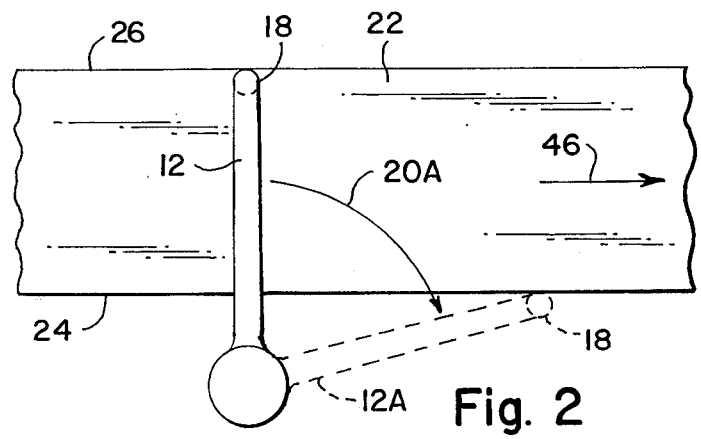
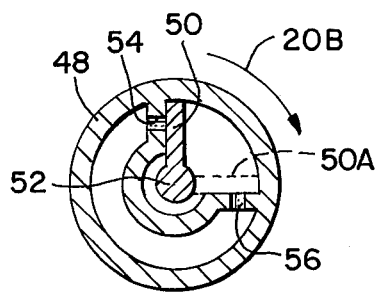
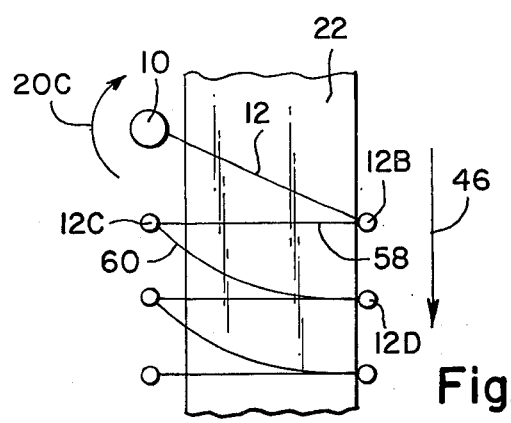
Fig. 1
Fig. 2
Fig. 3
Fig. 4

WEB PROCESS CONTROL APPARATUS

BACKGROUND OF THE INVENTION

1. THE FIELD OF THE INVENTION

This invention relates to a web process control and detection apparatus, and more particularly to that class utilizing moving sensors and detectors across the surfaces of the web as the web is being transported in a direction parallel to the longitudinal marginal edges of the web.

2. DESCRIPTION OF THE PRIOR ART

The prior art abounds with apparatus utilized to measure web characteristics as the web travels in the direction of web processing.

U.S. Pat. No. 3,190,261, issued on June 22, 1965 to G. F. Ziffer teaches a pair of web measuring devices comprising a detector and a source mounted on the three ends of a U-shaped structure travelling horizontally across the surface, travelling transverse to direction of travel of a web and spanning the upper and lowermost surfaces thereof.

U.S. Pat. No. 3,332,279, issued on July 25, 1967 to D. J. Tompos et al, discloses a similar pair of electronic units which travel directly transverse to web direction utilizing a beam as a support therefore. A light sensing apparatus detects when the sensors reach the marginal edge of the web and cause the opening of the sensor above the uppermost surface of the web thereby preventing tearing of the web due to a closely located sensor face as the sensor face passes from beyond the marginal edge to a position directly over the web. Both aforementioned inventions, though completely scanning the web from edge to edge in a transverse direction, suffer a common deficiency in being unable to provide directly a linear output directly transverse to the web direction, and utilize a comples mechanical probe positioning device which, due to its reciprocating ability, creates undue vibration and complicated and expensive transporting mechanisms therefore.

SUMMARY OF THE INVENTION

The primary object of the instant invention is to provide a scanning measuring apparatus which utilizes rotary motion as opposed to reciprocating motion therefore.

Another object of the instant invention is to provide a web sensing apparatus which yields, if desired, web characteristics directly proportional to a distance measurement made transverse to the direction of web travel.

Still another object of the instant invention is to provide a reciprocating apparatus utilizing rotary motion to control a portion of the web to be scanned, thereby taking advantage of the many linkage mechanisms providing a variety of rotary motions.

A further object of the instant invention is to provide an apparatus for scanning characteristics of paper or other web-like materials whose opposing detector and scanning devices may be adjusted at varying distances apart utilizing a portion of the apparatus which is permanently mounted outside and away from one marginal edge of the apparatus.

Another object of the instant invention is to provide a scanning and detecting means utilizing electrical conductors connected thereto which undergo a minimum of stress as the scanner and detector moves across the surface of the web to be measured.

Web processing control and measurement heretofore employ bulk measuring detectors which averaged out the characteristic to be measured by sensing the overall characteristics of a web in a discreet band transverse to the width of the web or made a series of independent measurements as a small area scanning device sensitive to a source device where both simultaneously move across portions of the web, usually in a direction transverse to web travel. Unfortunately such apparatus yields gross information concerning the web characteristics to be measured or in the latter case yields a signal output representing measurement made across the web describing a sensing path which is triangular in shape, due to the continual motion of the web as it is being measured.

The instant invention utilizes a pair of swinging arms, as opposed to a pair of reciprocating arms, the swinging arms pivoting about a pivot axis normal to the plane of the surfaces of the web pivoting about a point located adjacent one marginal edge of the web. The arms connecting the pivot axis and the sensor detector heads mounted at the free ends thereof have a length substantially equal to the width of the web and are rotated approximately ninety degrees thereby covering the entire width of the web as the web travels. If the rotation of the arms is other than linear, the path taken by the scanning source and the scanner may transcribe a straight line running transverse to the direction of web travel, a feat unattainable heretofore, and yielding, thereby, an output directly representative of a measurement transverse to direction of web travel. This linear transverse measurement is useful in setting the net of rollers used in polishing paper, or in applying coatings, or other processing apparatus in web treatment and preparation.

Alternatively, if the rotation of the arms is not linear the arms will travel across the surface of the web transposing their position from edge to edge thereof, and yielding an output signal representative of web characteristics nevertheless. Utilizing a rotating motion enhances the simplicity of the coupling arrangements to the transducer and sensing apparatus mounted at the free end of the arms whilst eliminating the complexity of installation of such a measurement apparatus.

These objects, as well as other objects, of this invention will become readily apparent after reading the following description of the accompanying drawings.

BRIEF DESCRIPTION OF THE DRAWINGS

FIG. 1 is a perspective view of the instant invention including a portion of a web and the associate measuring or control apparatus console.

FIG. 2 is a plan view of the instant invention shown in transverse position across a portion of a moving web.

FIG. 3 is a pneumatically operated air cylinder utilized to obtain ninety degree rotation of the arm element shown in FIG. 2.

FIG. 4 is a plan of a segment of travelling web in a pattern of scanning obtainable by utilizing the instant invention.

DESCRIPTION OF THE PREFERRED EMBODIMENT

The structure and method of fabrication of the present invention is applicable to a post erected substantially normal to the plane of the surface of the web and located adjacent one marginal edge thereof outward of the web face itself. A pair of arms are connected to each other in such a way that the longitudinal axis of each arm is parallel to the other but may be disposed varying distances apart, having the interior faces thereof opposite each face of the web, attached to the arms, at the free ends thereof, the transducers of conventional type and senses responsive to the transducers, such as a source of X-ray emanations, an X-ray detector or such as a pair of electrodes sensitive to the capacity of the web. Both arms are pivoted about the longitudinal axis of the post utilizing a pivot mechanism such as a rotating pneumatic cylinder whose output shaft is connected to each arm utilizing a spline therefore. Each arm may be moved up and down along the post by turning a collar upon which the arm rests upon threads located on the outside of the post. Thus, the spacing of the detector and source apparatus at the free ends of the arms may be adjusted varying distances away from the adjacent face of the web. Wires interconnecting the source and detector apparatus and a control or measurement console device undergo a minimum of stress because of the small amount of rotation and transposition thereof due to the ninety degree rotatable motion of the arms.

Now referring to the FIGURES, and more particularly to the embodiment illustrated in FIG. 1 showing post 10 upon which arms 12 and 14 are pivotably secured. Arms 12 and 14 move in unison so that source 16 and detector 18 pivot about post 10 in a direction of arrow 20, enabling electronic apparatus 16 and 18 to transpose position along web 22 from edge 24 to edge 26 thereby. Pivot axis 28 describes the center of rotation of arms 12 and 14, which can be adjusted varying distances from the faces of web 22 utilizing ring 30 and ring 32 therefore. Ring 30 has internal threads engaging threads 34 located on the exterior surfaces of post 10. Arm 12 rests on the upper edge of ring 30 and is positioned upwardly in the direction of arrow 36 or downwardly in the direction of arrow 38 when ring 30 is rotated in a direction of arrows 20. Similarly, ring 32 controls the position of arm 14. Wires 40 bring the signal from sensing unit 18 to control console or measuring apparatus 42. Wires 44 provide source energy to source 16 from a suitable power supply, located within console 42. Web 22 travels in the direction of arrow 46 continuously as arm 12 and 14 rotate above pivot axis 28.

FIG. 2 illustrates web 22 travelling in the direction of arrow 46. Arm 12 is shown directly transverse the direction of web travel and is free to rotate in the direction of arrow 20A into a position denoted as 12A where sensor 18 is off edge 24 of web 22.

FIG. 3 illustrates a rotary cylinder 48 having a moving rotating plate 50 pivoted about shaft 52. Plate 50 rotates in the direction of arrow 20B dependent upon the application of pneumatic or hydraulic fluids introduced through port 54, causing plate 50 to move to the position denoted in phantom as 54A. Introduction of a pressurized fluid in port 56, when port 54 is vented, enables plate 50A to return to the position denoted by numerals 50, thereby causing shaft 52 to rotate 90°. Shaft 52 can be connected to arms 12 and 14, as shown in FIG. 1, utilizing a spline thereon so as to rotate the arms while allowing them to separate or close the distance that separates them.

FIG. 4 illustrates a post 10, an arm 12 pivotably secured thereto. Arrow 200 causes arm 12 to move in clockwise rotation downwardly and leftwardly from the position shown, and web 22 moves in the direction of arrow 46. The end of arm 12 denoted by numeral 12B can move in a transverse direction to web 22, symbolized by line 58. Line 58, as shown, is directly transverse to the direction of web travel 46 and allows thereby source 16 and sensor 18 to produce an output signal directly proportional to the characteristics of the web to be measured in a linear fashion transverse to web travel direction, until point 12B reaches point 12C. Then, due to the retracting nature of the rotation arm 12 counter to the direction of arrow 20C, curved line 60 is described by point 12C in reaching point 12D. This curved sensing zone along the surface of the paper, described by line 60, may be discarded, or, if desired, may be utilized taking into account the curved nature thereof by suitable adjustment within console 42, as shown in FIG. 1.

One of the advantages is a scanning measuring apparatus which utilizes rotary motion as opposed to reciprocating motion therefore.

A further advantage is a web sensing apparatus which yields, if desired, web characteristics directly proportional to a distance measurement made transverse to the direction of web travel.

Another advantage is a reciprocating apparatus utilizing rotary motion to control a portion of the web to be scanned, thereby taking advantage of the many linkage mechanisms providing a variety of rotary motions.

Still another advantage is an apparatus for scanning characteristics of paper or other web-like materials whose opposing detector and scanning devices may be adjusted at varying distances apart utilizing a portion of the apparatus which is permanently mounted outside and away from one marginal edge of the apparatus.

A further advantage is a scanning and detecting means utilizing electrical conductors connected thereto which undergo a minimum of stress as the scanner and detector moves across the surface of the web to be measured.

Thus, there is disclosed in the above description and in the drawings, an embodiment of the invention which fully and effectively accomplishes the objects thereof. However, it will be apparent, to those skilled in the art, how to make variations and modifications to the instant invention. Therefore, this invention is to be limited not by the specific disclosure herein, but only by the appending claims.

I claim:

1. A process control and measuring apparatus comprising a pair of parallel arms disposed in spaced apart relationship, a web travelling between said arms, said arms commonly pivotably secured to a shaft, said shaft having the longitudinal axis thereof disposed perpendicular to the surface of said plane, said arms describing substantially a ninety degree arc at the free ends thereof, said arc passing about the surfaces of said web, measuring means fixedly secured to a free end of one of said arms, coupling means for coupling the signal generated by said measuring means to a point remote from said shaft post.

2. The process control and measuring apparatus as claimed in claim 1 wherein said arms are pivoted about said post utilizing a non-linear rotational motion therefore, said non-linear rotational motion providing a scanning path for said detector which is transverse to the direction of web travel.

3. The process control and measuring apparatus as claimed in claim 1 wherein said arms pivot about said postal line substantially 90°.

4. The process control and measuring apparatus as claimed in claim 1 wherein a liquid operated cylinder providing rotating motion is coupled to said arms, said coupling includes a spline shaft therefore engaging the end of said arms pivotably secured to said post.

* * * * *